(12) United States Patent
Sabelko et al.

(10) Patent No.: US 8,658,145 B2
(45) Date of Patent: Feb. 25, 2014

(54) LOW MOLECULAR WEIGHT AMPHOLYTIC POLYMERS FOR PERSONAL CARE APPLICATIONS

(75) Inventors: Jobiah J. Sabelko, Sugar Grove, IL (US); Jeffrey R. Cramm, Batavia, IL (US); Damyanti J. Patel, Hoffman Estates, IL (US)

(73) Assignee: The Lubrizol Corporation, Wickliffe, OH (US)

( * ) Notice: Subject to any disclaimer, the term of this patent is extended or adjusted under 35 U.S.C. 154(b) by 822 days.

(21) Appl. No.: 12/534,221

(22) Filed: Aug. 3, 2009

(65) Prior Publication Data

US 2009/0291053 A1 Nov. 26, 2009

Related U.S. Application Data

(62) Division of application No. 11/369,044, filed on Mar. 6, 2006, now abandoned.

(51) Int. Cl.
*A61K 8/81* (2006.01)
*A61Q 5/12* (2006.01)

(52) U.S. Cl.
CPC .............. *A61K 8/8194* (2013.01); *A61Q 5/12* (2013.01)
USPC ..................................... 424/70.16

(58) Field of Classification Search
None
See application file for complete search history.

(56) References Cited

U.S. PATENT DOCUMENTS

| | | |
|---|---|---|
| 2,438,091 A | 3/1948 | Lynch et al. |
| 2,528,378 A | 10/1950 | Manheimer et al. |
| 2,658,072 A | 11/1953 | Kosmin et al. |
| 3,769,398 A | 10/1973 | Hewitt et al. |

(Continued)

FOREIGN PATENT DOCUMENTS

| | | |
|---|---|---|
| EP | 0521665 A1 | 1/1993 |
| FR | 2849774 A1 | 7/2004 |
| WO | WO 02/40622 A2 | 5/2002 |
| WO | WO 02/40622 A3 | 5/2002 |

*Primary Examiner* — Brian Gulledge
(74) *Attorney, Agent, or Firm* — Christopher P. Demas, Esq.; Michael F. Esposito, Esq.

(57) ABSTRACT

A cosmetically acceptable composition comprising from about 0.1 to about 10 weight percent, based on polymer solids, of a water-soluble ampholyte polymer comprising: from at least 1 to as much as 95 weight percent of the nonionic monomer acrylamide; from at least 5 to as much as 80 weight percent of the cationic monomer dimethyldiallylammonium chloride; from at least 1 to as much as 75 weight percent of the anionic monomer acrylic acid, is disclosed. The application of these polymers to a keratinous substance is also disclosed. In addition, a method of treating a keratinous substance comprising applying a cosmetically acceptable composition comprising from about 0.1 to about 10 weight percent, based on polymer solids, of an ampholyte polymer produced by the following process: (1) preparing a monomer solution containing: from at least 1 to as much as 95 weight percent of the nonionic monomer acrylamide; from at least 5 to as much as 80 weight percent of the cationic monomer dimethyldiallylammonium chloride; from at least 1 to as much as 75 weight percent of the anionic monomer acrylic acid; (2) providing a reactor and water to said reactor; (3) optionally charging said reactor with a sequestering agent, a chain transfer agent or a combination thereof; (4) purging said reactor to remove oxygen from said reactor; (4) heating the contents of said reactor; and (5) feeding said monomer solution and initiator solution into said reactor, is disclosed.

10 Claims, 1 Drawing Sheet

(56) References Cited

U.S. PATENT DOCUMENTS

| | | |
|---|---|---|
| 5,275,809 A | 1/1994 | Chen et al. |
| 5,296,218 A | 3/1994 | Chen et al. |
| 5,338,541 A | 8/1994 | Matz et al. |
| 5,573,709 A | 11/1996 | Wells |
| 5,609,862 A * | 3/1997 | Chen et al. ................ 424/70.11 |
| 6,210,689 B1 | 4/2001 | Martino et al. |
| 6,627,776 B2 | 9/2003 | Walele et al. |
| 2006/0254000 A1 | 11/2006 | Ducheron et al. |

\* cited by examiner

LOW MOLECULAR WEIGHT AMPHOLYTIC POLYMERS FOR PERSONAL CARE APPLICATIONS

CROSS REFERENCE TO RELATED APPLICATION

This application is a continuation of U.S. Ser. No. 11/369,044, which is herein incorporated by reference.

FIELD OF THE INVENTION

This invention relates to low molecular weight ampholytic polymers and uses thereof. More specifically, this invention relates to cosmetically acceptable compositions containing low molecular weight polymers and their use in the personal care industry.

SUMMARY OF THE INVENTION

The surface properties of human hair, skin and nails are of basic interest in cosmetic science, and there has thus been a long-standing desire to discover cosmetic compositions, which will beneficially affect the topical and bulk condition of these keratinous substrates. Such compositions should have adequate adherent properties, so that they are not only absorbed initially, but are also retained on exposure to water. This ability to be absorbed onto the substrate and to resist water rinse off is referred to as substantivity.

Compositions for treating hair should improve the wet and dry combability of the hair, facilitate detangling in wet hair combing and reduce static flyaway in dry hair combing while also imparting softness and suppleness to the hair. Ingredients used in shampoos should impart improved foam stability to the shampoo while hair fixative compositions should impart properties such as good curl retention without having a deleterious effect on wet combability.

With respect to compositions for treating skin, compositions are desired which will function to improve such properties as retention of skin moisture, softening of the skin, attraction of air moisture, retardation of skin water loss, feel and reduction of skin irritations caused by contact with detergents, soaps and the like. Compositions for treating nails should strengthen or harden fragile or brittle nails and improve the overall appearance of the nails.

The prior art, in particular U.S. Pat. No. 5,296,218 to Chen et al., which is herein incorporated by reference, discloses ampholyte terpolymer conditioning additives for hair care products which improve wet and dry hair combability, especially detangling and reduced static flyaway, sheen, and fixative properties, especially curl retention. In particular, ampholyte terpolymers that have a weight average molecular weight of from about 10 thousand to 10 million, and comprise (a) from at least 1 to as much as 95 weight percent of the nonionic monomer acrylamide, (b) from at least 5 to as much as 80 weight percent of the cationic monomer dimethyldiallylammonium chloride, and (c) from at least 1 to as much as 75 weight percent of the anionic monomer acrylic acid are disclosed.

The present invention pertains to ampholytic polymers that have improved performance characteristics over the prior art.

SUMMARY OF THE INVENTION

The present invention provides for a cosmetically acceptable composition comprising from about 0.1 to about 10 weight percent, based on polymer solids, of a water-soluble ampholyte polymer comprising:

(a) from at least 1 to as much as 95 weight percent of the nonionic monomer acrylamide of the following formula:

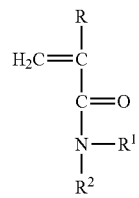

where R is H or $CH_3$; and $R^1$ and $R^2$ are independently H, $C_{1-4}$ alkyl, $CH_2{}_2OCH_3$, $CH_2OCH_2CH(CH_3)_2$, $(CH_2CH_2O\text{---})_x\text{---}H$, where $x=1\text{-}50$, or phenyl, or together are $C_{3-6}$ cycloalkyl;

(b) from at least 5 to as much as 80 weight percent of the cationic monomer dimethyldiallylammonium chloride of the following formula:

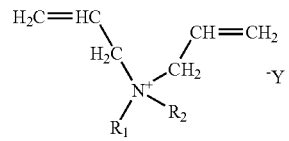

where $R_1$ and $R_2$ are independently H or $C_{1-12}$ alkyl, and the moiety $^-Y$ is a suitable anion;

(c) from at least 1 to as much as 75 weight percent of the anionic monomer acrylic acid of the following formula:

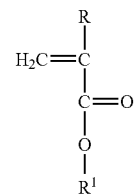

where R is H or $CH_3$; and $R^1$ is $X^+$, H, and $X^+$ is a suitable cation forming a salt of the carboxylic acid; and wherein the weight average molecular weight of said polymer is from about 5 thousand to about 250,000.

Cosmetic compositions comprising the polymers of this invention may be applied to keratinous substances.

The present invention also provides for a method of treating a keratinous substance comprising applying a cosmetically acceptable composition comprising from about 0.1 to about 10 weight percent, based on polymer solids, of an ampholyte polymer produced by the following process:

(1) preparing a monomer solution containing:

(a) from at least 1 to as much as 95 weight percent of the nonionic monomer acrylamide of the following formula:

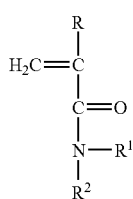

where R is H or $CH_3$; and $R^1$ and $R^2$ are independently H, $C_{1-4}$ alkyl $CH_2OCH_3$, $CH_2OCH_2CH(CH_3)_2$, $(CH_2CH_2O-)_x$, —H, where x=1-50, or phenyl, or together are $C_{3-6}$ cycloalkyl;

(b) from at least 5 to as much as 80 weight percent of the cationic monomer dimethyldiallylammonium chloride of the following formula:

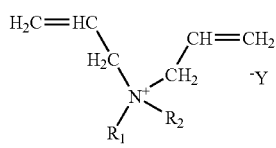

where $R_1$ and $R_2$ are independently H or $C_{1-12}$ alkyl, and the moiety $^-Y$ is a suitable anion;

(c) from at least 1 to as much as 75 weight percent of the anionic monomer acrylic acid of the following formula:

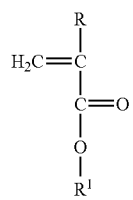

where R is H or $CH_3$; and $R^1$ is $X^+$, H, and $X^+$ is a suitable cation forming a salt of the carboxylic acid;

(2) providing a reactor and water to said reactor;
(3) optionally charging said reactor with a sequestering agent, a chain transfer agent or a combination thereof;
(3) purging said reactor to remove oxygen from said reactor;
(4) heating the contents of said reactor; and
(5) feeding said monomer solution and initiator solution into said reactor.

DETAILED DESCRIPTION OF THE INVENTION

Figure 1:
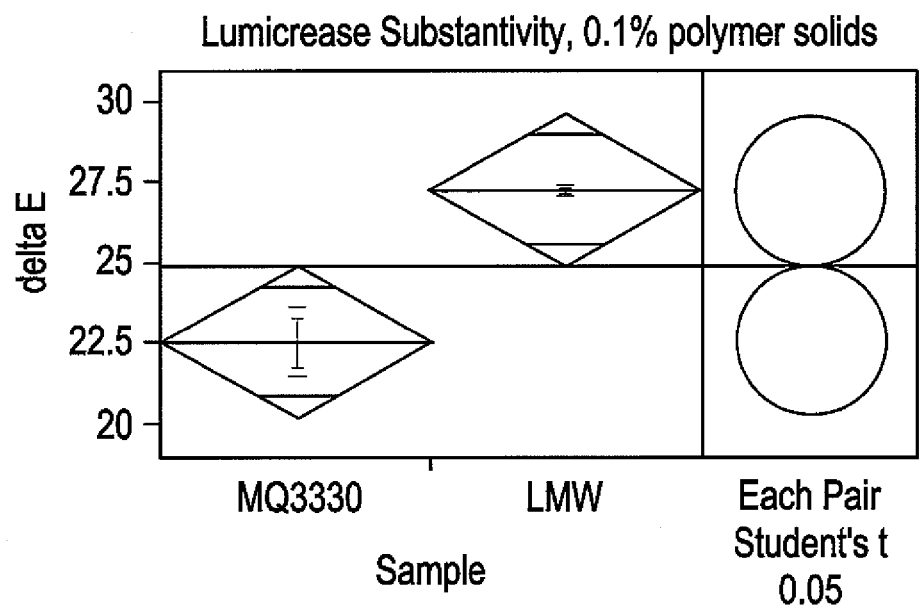
FIG. 1 shows Lumicrease data for both Merquat® 3330 (available from Nalco Company, Naperville, Ill.) that has a weight average molecular weight of approximately 1,500,000 and LMW that has a weight average molecular weight of approximately 150,000.

The following abbreviations shall have the following meanings: "DADMAC": diallyldimethylammonium chloride; "PVP": polyvinyl pyrrolidone; "MEA": monoethanolamide; "DEA": diethanolamide; "USP": United States Pharmacopia; "PVMMA": polymethyl vinyl ether/maleic anhydride; "NF": National Formulary; "PABA": p-amino benzoic acid; "AMP": amino methyl propane; and "VA": vinyl acetate; and "GPC": gel permeation chromatography.

"LMW" means a low molecular weight polymer of one embodiment of the present invention, wherein said weight average molecular weight is approximately 150,000.

Weight average molecular weight of the present invention was determined by GPC.

The cosmetically acceptable composition of this invention comprises from about 0.1 to about 10 weight percent, based on polymer solids, of an ampholyte polymer comprising:

(a) from at least 1 to as much as 95 weight percent of the nonionic monomer acrylamide of the following formula:

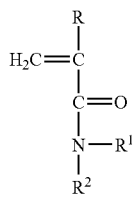

where R is H or $CH_3$; and $R^1$ and $R^2$ are independently H, $C_{1-4}$ alkyl, $CH_2OCH_3$, $CH_2OCH_2CH(CH_3)_2$, $(CH_2CH_2O-)_x$—H, where x=1-50, or phenyl, or together are $C_{3-6}$ cycloalkyl;

(b) from at least 5 to as much as 80 weight percent of the cationic monomer dimethyldiallylammonium chloride of the following formula:

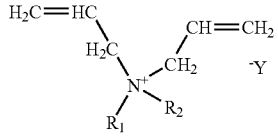

where $R_1$ and $R_2$ are independently H or $C_{1-12}$ alkyl and the moiety $^-Y$ is a suitable anion;

(c) from at least 1 to as much as 75 weight percent of the anionic monomer acrylic acid of the following formula:

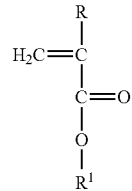

where R is H or $CH_3$; and $R^1$ is $X^+$, H, and $X^+$ is a suitable cation forming a salt of the carboxylic acid; and wherein the weight average molecular weight of said polymer is from about 5 thousand to about 250,000.

In one embodiment, the cosmetically acceptable composition has weight average molecular weight of from about 78,000 to about 165,000.

In another embodiment, the cosmetically acceptable composition has a weight average molecular weight of about 150,000.

In another embodiment, the various polymer compositions of the claimed invention contain acrylamide that is from about 10 to about 80 weight percent, dimethyldiallylammonium chloride that is from about 15 to about 60 weight percent, and acrylic acid that is from about 5 to about 40 weight percent.

In addition to the ampholytic polymer, the cosmetically acceptable composition of this invention may include surface-active agents. Surface active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used in this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of about 12 to about 16 carbon atoms and an average degree of ethoxylation of about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinanrate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surface-active agents which may be used in the cosmetically acceptable composition of this invention include derivatives of aliphatic secondary and tertiary amines, in which the aliphatic substituent contains about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL™ as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Quaternary ammonium compounds can also be used in the cosmetically acceptable composition of this invention as long as they are compatible in the compositions of the invention. Cationic surface-active agents generally include, but are not limited to fatty quaternary ammonium compounds containing about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: behentrimonium chloride, cocotrimonium chloride, cethethyldimonium bromide, dibehenyldimonium chloride, dihydrogenated tallow benzylmonium chloride, disoyadimonium chloride, ditallowedimonium chloride, hydroxycetyl hydroxyethyl dimonium chloride, hydroxyethyl behenamidopropyl dimonium chloride, hydroxyethyl cetyldimonium chloride, hydroxyethyl tallowedimonium chloride, myristalkonium chloride, PEG-2 oleamonium chloride, PEG-5 stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The cosmetically acceptable compositions may include di-long chain amines about $C_{10}$ to $C_{22}$, long chain fatty amines about $C_{10}$ to $C_{22}$, and mixtures thereof. Specific examples include dipalmitylamine, lauramidopropyldimethyl, stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable composition of this invention include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH $(CH_2)_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount about 0.1 to 50 percent by weight, preferably about 0.5 to about 40 percent by weight, more preferably about 1 to about 20 percent by weight.

The cosmetically acceptable composition of this invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of about 0.5 to about 40 percent by weight, preferably about 0.5 to about 20 percent by weight and more preferably about 0.5 to about 12 percent by weight.

The cosmetically acceptable composition of this invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, sythetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning®, Midland, Mich., USA. Additional alkyl and phenyl silicones may be employed to enhance moisturizing properties. Resins such as dimethicone (and) trimethylsoiloxysilicate, known as Dow Corning® 593 or Cyclomethicone (and) Trimethylsiloxysilicate, known as Dow Corning® 749 fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention may also include silicone compounds. Preferably, the viscosity of the silicone component at a temperature of 25° C. is about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane endblocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of this invention may include volatile and non-volatile silicone oils or fluids. The silicone compounds can be either linear or cyclic polydimethylsiloxanes with a viscosity of about 0.5 to about 100 centistokes. The most preferred linear polydimethylsiloxane compounds have a range of about 0.5 to about 50 centistokes. One example of a linear, low molecular weight, volatile polydimethylsiloxane is octamethyltrisiloxane, available under the trade name Dow Corning® 200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of this invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity of about 2.0 to about 7.0 centistokes, and mixtures thereof. Preferred cyclomethicones are available from Dow Corning, Midland, Mich., USA under the trade names Dow Corning® 244 fluid, Dow Corning® 245 fluid, Dow Corning® 246, Dow Corning® 344 fluid and Dow Corning® 345 fluid, and Silicone SF-1173 and Silicone SF-1202 from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols, Dow Corning® 3225C and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol, known as Dow Corning® 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munich, Germany. When used, the silicone surfactants are preferably included in the formulations of this invention at a concentration of 0.1 to 30 weight percent, more preferably 1 to 15 weight percent.

Amine functional silicones and emulsions may be utilized in the present invention. Preferred examples include Dow Corning® 8220, Dow Corning® 939, Dow Corning® 949, Dow Corning® 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions of this invention may include volatile hydrocarbon oils. The volatile hydrocarbon comprises from about $C_6$ to $C_{22}$ atoms. A preferred volatile hydrocarbon is an aliphatic hydrocarbon having a chain length of about $C_6$ to $C_{16}$ carbon atoms. An example of such compound includes isohexadecane, under the trade name Permethyl 101A, available from Presperse, South Plainfield, N.J., USA. Another example of a preferred volatile hydrocarbon is $C_{12}$ to $C_{14}$ isoparaffin, under the trade name Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of this invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17$^{th}$ Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47, Polyquaternium-53, Polyquaternium-55 and polymethacrylamidopropyltrimonium chloride, and mixtures thereof. When used, the conditioning polymers are preferably included in the cosmetically acceptable composition of this invention at a concentration of about 0.1 to 10 weight percent, preferably about 0.2 to about 6 weight percent and most preferably about 0.2 to about 5 weight percent.

The cosmetically acceptable composition of this invention may include one or more Theological modifiers. The rheological modifiers which can be used in this invention include, but are not limited to high molecular weight crosslinked homopolymers of acrylic acid, and acrylates/$C_{10-30}$ alkyl acrylate crosspolymer, such as the Carbopol® and Pemulen® series, both available from Noveon, Inc, Cleveland, Ohio, USA; anionic acrylate polymers such as Salcare® AST and cationic acrylate polymers such as Salcare® SC96, available from Ciba Specialties, High Point, N.C., USA; acrylamidopropylttrimonium chloride/acrylamide; hydroxyethyl methacrylates polymers, Steareth-10 Allyl Ether/Acrylate Copolymer; Acrylates/Beheneth-25 Metacrylate Copolymer, known as Aculyn® 28, available from International Specialties, Wayne, N.J., USA; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of about 0.01 to about 12 weight percent, preferably about 0.05 to about 10 weight percent and most preferably about 0.1 to about 6 weight percent.

The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The antioxidants will be present at about 0.01 to about 5 weight percent, preferably about 0.1 to about 3 weight percent and most preferably about 0.2 to about 2 weight percent of the cosmetically acceptable composition.

The cosmetically acceptable composition of this invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis(hydroxypropyl)aminobenzoate, 2-ethylhexy 1-2-cyano-3,3-diphenylacrylate, homomethyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and typically is about 0.1 to about 10 percent by weight, preferably about 2 to about 8 percent by weight.

The cosmetically acceptable composition of this invention may include one or more preservatives. Example of preservatives, which may be used include, but are not limited to 1,2-dibromo-2,4-dicyano butane (Methyldibromo Glutaronitrile, known as MERGUARD®, Nalco Company, Naperville, Ill., USA), benzyl alcohol, imidazolidinyl urea, 1,3-bis-(hydroxymethyl)-5,5-dimethyl-2,3-imidazolidinedione (e.g., DMDM Hydantoin, known as GLYDANT®, Lonza, Fairlawn, N.J., USA.), methylchloroisothiazolinone and methylisothiazolinone (e.g., Kathon®, Rohm & Haas Co., Philadelphia, Pa., USA), methyl paraben, propyl paraben, phenoxyethanol, and sodium benzoate, and mixtures thereof.

The cosmetically acceptable composition of this invention may include any other ingredient normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the cosmetically acceptable composition of this invention. The treated pigments are then more effective as sunscreen actives and for use in color cosmetics such as make up and mascara.

The cosmetically acceptable composition of this invention can be presented in various forms. Examples of such forms include, but are not limited a solution, liquid, cream, emulsion, dispersion, gel, thickening lotion.

The cosmetically acceptable composition of this invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70 percent by weight, for example about 0.1 to about 70 percent by weight, relative to the weight of the total composition.

The cosmetically acceptable composition of this invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable composition of this invention also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

One or more cosmetically acceptable excipients may be added in conjunction with the polymer of the claimed invention. In another embodiment of this invention, the cosmetically acceptable composition further comprises one or more excipients selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines of about $C_{10}$ to $C_{22}$, long chain fatty amines of about $C_{10}$ to $C_{22}$, fatty alcohols, ethoxylated fatty alcohols and di-tail phospholipids.

In another embodiment of this invention, the cosmetically acceptable composition is selected from the group consisting of shampoos, aftershaves, sunscreens, lotions, hand and body creams, liquid soaps, bar soaps, bath oil bars, shaving creams, dishwashing liquids, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, temporary and permanent hair colors, color conditioners, hair tighteners, coloring and non-coloring hair rinses, hair tints, hair wave sets, permanent waves, curling, hair straighteners, hair grooming aids, hair tonics, hair dressings and oxidative products, spritzes, styling waxes and balms.

A method of treating a keratinous substance is also claimed. In particular a method of treating a keratinous substance by applying a cosmetically acceptable composition comprising from about 0.1 to about 10 weight percent, based on polymer solids, of an ampholyte polymer comprising:

(a) from at least 1 to as much as 95 weight percent of the nonionic monomer acrylamide of the following formula:

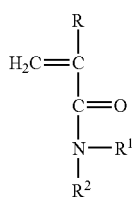

where R is H or $CH_3$; and $R^1$ and $R^2$ are independently H, $C_{1-4}$ alkyl, $CH_2OCH_3$, $CH_2OCH_2CH(CH_3)_2$, $(CH_2CH_2O-)_x-H$, where x=1-50, or phenyl, or together are $C_{3-6}$ cycloalkyl;

(b) from at least 5 to as much as 80 weight percent of the cationic monomer dimethyldiallylammonium chloride of the following formula:

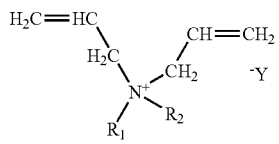

where $R_1$ and $R_2$ are independently H or $C_{1-12}$ alkyl, and the moiety $^-Y$ is a suitable anion;

(c) from at least 1 to as much as 75 weight percent of the anionic monomer acrylic acid of the following formula:

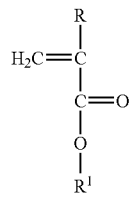

where R is H or $CH_3$; and $R^1$ is $X^+$, H, and $X^+$ is a suitable cation forming a salt of the carboxylic acid; and wherein the weight average molecular weight of said polymer is from about 5 thousand to about 250,000.

In one embodiment the keratinous substance is hair or skin.

In another embodiment, the cosmetically acceptable composition applied to keratinous substance has a weight average molecular weight of from about 78,000 to about 165,000.

In another embodiment, the cosmetically acceptable composition has a weight average molecular weight of about 150,000.

In another embodiment, the cosmetically acceptable composition applied to the keratinous substance contains acrylamide that is from about 10 to about 80 weight percent, dimethyldiallylammonium chloride that is from about 15 to about 60 weight percent, and acrylic acid that is from about 5 to about 40 weight percent.

Compositions for treating skin include leave-on or rinse-off skin care products such as lotions, hand/body creams, shaving gels or shaving creams, body washes, sunscreens, liquid soaps, deodorants, antiperspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions of this invention may be prepared as either oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, the humectant, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

The condition and appearance of the hair can be improved by applying a composition that conditions or softens the hair and/or helps maintain the hair in a particular style or shape. Different vehicles have been utilized for setting the hair including lotions, gels, mousses, waxes, creams, balms, styling sprays and hair sprays. These compositions are all formulated with polymeric resins as the traditional materials to impart curl retention and stiffness. In "The History of Polymers in Haircare," Cosmetics and Toiletries, Volume 103, December 1988, R. Y. Lochhead discusses many synthetic polymers that have been used in creating styling aids.

The general principles relative to the hair styling and setting are discussed in detail by Zviak, in The Science of Hair Care, Marcel Dekker, pp. 149-181 (1986) and by Dallal and Rochafort in Hair and Hair Care, Marcel Dekker, pp. 105-165 (1997). Zviak and Dallal and Rocafort review polymers used in hair styling products and the formulation principles used to produce a hair styling composition that provides such beneficial hair setting properties as curl retention, wet combing, body, bounce, stylability and control. In the formulation of any end-use hair styling product, examples show that some of these benefits must be sacrificed to some degree to achieve a competing benefit (such as good hold with smooth feel). Therefore, the formulation of hair styling compositions is often a compromise, striking the right balance of both hold and feel properties.

Compositions for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount about 3 to about 50 percent by weight, preferably about 3 to about 20 percent, and their pH is general in the range about 3 to about 10 percent.

Preferred shampoos of this invention contain combinations of anionic surfactants with zwitterionic surfactants and/or amphoteric surfactants. Especially preferred shampoos contain 0 to about 16 percent active of alkyl sulfates, 0 to about 50 weight percent of ethoxylated alkyl sulfates, and 0 to about 50 weight percent of surface-active agents selected from the nonionic, amphoteric, and zwitterionic surface-active agents, with at least 5 weight percent of either alkyl sulfate, ethoxylated alkyl sulfate, or a mixture thereof, and a total surfactant level of about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples include the Polyquaterniums (example Polyquaternium-1 to Polyquaternium-67), Guar Hydroxypropyl Trimonium Chloride, Starch Hydroxypropyl Trimonium Chloride and Polymethacrylamidopropyl Trimonium Chloride.

Other preferred compositions are used in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially resins, acrylates and acrylic acid thickeners such as those available from Noveon/Lubrizol; xanthan gums; sodium alginates; gum arabic; cellulose derivatives and poly (ethylene oxide) based thickeners, and it is also possible to achieve thickening by means of a mixture of polyethylene glycol stearate or distearate or by means of a mixture of a phosphoric acid ester and an amide. The concentration of thickener is generally about 0.05 to about 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of about 0.25 to about 10 percent by weight. Any additional hair fixative resin(s) can be selected from the following group, as long as the resin is compatible with a given polymer of the present invention. This group consists of: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. In "The History of Polymers in Haircare," Cosmetics and Toiletries, Volume 103, December 1988, R. Y. Lochhead discusses many synthetic polymers that have been used in creating styling aids and is incorporated herein by reference.

The hair styling compositions of this invention are applied to wet or dry hair by spraying or by rubbing onto the hair manually. The treated hair is then mechanically fixed in the desired configuration using, for example, any of a variety of rollers or curlers. In the case of application to wet hair, the hair is then dried using ambient air, electric or hot air drying using, for example, a blow dryer. The hair is then combed to provide the desired hairstyle.

Saccharides may be used to thicken, enhance aesthetics and provide extra conditioning, feel or curl retention benefits or other formulation benefits. Saccharides which may be used in the present invention include nonionic or cationic saccharides such as agarose, amylopectins, amyloses, arabinans, arabinogalactans, arabinoxylens, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitins, chitins, chitosan, chitosan pyrrolidone carboxylate, chitosan glycolate chitosan lactate, cocodimonium hydroxypropyl oxyethyl cellulose, colominic acid (poly(N acetyl-neuraminic acid)), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomannans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer *Encyclopedia of Chemical Technology*, Fourth Edition, Vol. 16, John Wiley and Sons, NY pp. 578-611 (1994) which is incorporated entirely by reference. Complex carbohydrates found in Kirk-Othmer *Encyclopedia of Chemical Technology*, Fourth Edition, Vol. 4, John Wiley and Sons, NY pp. 930-948, 1995 which is incorporated herein by reference.

The foregoing may be better understood by reference to the following Examples, which are presented for purposes of illustration and are not intended to limit the scope of this invention.

EXAMPLE I

Preparation of the Ampholyte Polymers

A monomer feed polymerization process is used to control the molecular weight and composition of the polymer. The temperature is controlled by reflux. The monomer solution is made by mixing the desired amounts of deionized water, acrylamide (AM), acrylic acid (AA), and diallyldimethylammonium chloride (DADMAC). Sodium hydroxide is added to partially neutralize the acrylic acid. The total monomer concentration of this solution is about 50%. The initiator solution consists of about 25% ammonium persulfate in deionized water. The reactor is charged with deionized water containing small amounts of ethylenediamine tetraacetic acid (EDTA) to control trace metals and sodium formate to adjust polymer molecular weight. The reactor contents are purged with nitrogen gas to remove oxygen and heated to 80-100° C. At this point the initiator solution and the monomer solution are fed into the reactor. After the monomer feed is finished, the initiator feed is continued to complete the polymerization. After the polymerization is finished, a solution of sodium bisulfite is added to scavenge any residual acrylamide monomer. Specific examples of polymers produced are as follows:

a. 36.2:35.8:28 Mole % AM:AA:DADMAC

Deionized water (147.2 g), AM (215.5 g of a 49.4% aqueous solution), AA (106.5 g), and DADMAC (301.7 g of a 62% aqueous solution) were mixed in a monomer feed vessel. Sodium hydroxide (24.7 g of a 50% aqueous solution) was added to partially neutralize the AA. The pH of the resulting monomer solution was about 4.4. The initiator, ammonium persulfate (4.4 g), was dissolved in deionized water (13.2 g). A 1.5 liter polymerization reactor equipped with a stirrer and reflux condenser was charged with DI water (168.2 g), sodium formate (0.15 g) and EDTA (0.20 g). The pH of this solution was adjusted to about 6 with a small amount of HCl. The reactor contents were purged with nitrogen gas for 30 minutes to remove oxygen and heated to 90° C. At this point the feed of initiator solution to the reactor was started. The flow rate was adjusted for a total feed time of 150 minutes. As soon as the initiator flow was established, the feed of the monomer solution to the reactor was started. The flow rate of the monomer was adjusted for a total feed time of 120 minutes. The reactor contents were gradually warmed to 100° C. during the first 20 minutes of the monomer feed. The temperature was held at reflux (100-103° C.) for the remainder of the polymerization. After the monomer feed was finished, the initiator feed continued for about 30 minutes. After the initiator feed was complete, the polymer was stirred at 90-100° C. for 60 minutes to complete the polymerization. A solution of sodium metabisulfite (5.5 g) in DI water (12.8 g) was added to scavenge any residual acrylamide monomer. Appropriate cosmetically acceptable preservatives may be added after polymerization.

b. 40:31:29 Mole % AM:AA:DADMAC

Deionized water (95.5 g), AM (235.3 g of a 49.5% aqueous solution), AA (91.5 g), and DADMAC (309.8 g of a 62% aqueous solution) were mixed in a monomer feed vessel. Sodium hydroxide (30.5 g of a 50% aqueous solution) was added to neutralize 30% of the AA. The pH of the resulting monomer solution was about 4.5. The initiator, ammonium persulfate (4.4 g), was dissolved in deionized water (13.2 g). A 1.5 liter polymerization reactor equipped with a stirrer and reflux condenser was charged with DI water (200.0 g), about 8% of the above monomer solution (61 g), sodium formate (1.4 g) and EDTA (0.20 g). The reactor contents were purged with nitrogen gas for 30 minutes to remove oxygen and heated to 80° C. At this point about 8% of the above initiator solution was charged to the reactor. An exotherm ensued and the contents of the reactor were heated to 100° C. The remaining monomer solution was fed into the reactor over 110 minutes while the remaining initiator solution was fed into the reactor over 140 minutes. During this time the temperature was held at reflux (100-103° C.). After the initiator feed was complete, the polymer was stirred at 90-100° C. for 60 minutes to complete the polymerization. A solution of sodium metabisulfite (5.5 g) in DI water (12.8 g) was added to scavenge any residual acrylamide monomer.

EXAMPLE II

Polymer Deposition/Substantivity: Lumicrease Dye Test

The Lumicrease Dye Test is often used in the personal care industry to measure the substantivity or deposition of materials onto keratin based substrates such as hair. The data provided below was collected using damaged bleached blonde hair as the test substrate. Damaged hair in contact with water at pH 6 carries negative charge sites. Cationic materials are therefore attracted to these negative charges on the hair surface and may deposit. When the cationic treated hair is then in turn introduced to a negatively charged red dye, the dye binds to the cationic sites imparting a red color to the hair tress. The intensity of the color indicates the level of deposition of the cationic material on the hair. The level of color intensity can be observed visually or more preferably quantified via use of a colorimeter or similar instrument. This general test is also referred to as the Rubine Dye Test as in its initial incarnation Rubine Dye was utilized (U.S. Pat. No. 3,769,398). However, Rubine Dye is no longer readily available and in this instance has been replaced by Lumicrease Bordeaux 3LR (Clariant). Many variants of the Lumicrease Dye Test exist in the literature (U.S. Pat. Nos. 6,627,776 and 6,210,689).

The data below was collected using the following general procedure. Bleached blonde hair tresses (6" length, 2.2 g) were washed using SLES, rinsed, and air-dried. Baseline color intensity of each tress was measured and recorded using a HunterLab Labscan XE colorimeter. Treatment solutions (500 mL) comprised of 0.1% polymer solids in water were prepared and adjusted to pH 6.0. A 0.1% solids Lumicrease Bordeaux 3LR dye solution was prepared using deionized water, adjusted to pH 2.65, and heated and maintained at 40° C. Hair tresses were treated with 0.1% polymer solution or control for 3 minutes and then immediately rinsed for 2 minutes with deionized water. Tresses were then immersed in 500 ml of heated dye solution for 1 minute and immediately rinsed under deionized water for 2 minutes. The tresses were allowed to air dry and then again measured using the calorimeter. Delta E values were calculated for each tress using the baseline and final readings.

FIG. 1 shows Lumicrease data for both Merquat® 3330, one of Nalco's traditional PQ-39 products, available from Nalco Company, Naperville, Ill., with weight average molecular weight of approximately 1,500,000 as determined by GPC and LMW that had a weight average molecular weight of approximately 150,000 as determined by GPC and which was prepared according to Example I(b) using a monomer charge comprised of 40 mole percent acrylamide, 31 mole percent acrylic acid and 29 mole percent DADMAC. The higher delta E value exhibited by the current invention indicates significantly higher polymer deposition and substantivity as compared to the traditional higher molecular weight PQ-39.

EXAMPLE III

Wet Hair Detangling/Combing: Combing Force Measurement

One of the primary consumer perceivables for hair care products is wet hair detangle/combing. The industry commonly uses combing force measurements obtained via Instron or similar instrumentation to quantify combing performance. In the work described here a Dia-Stron Mini Tensile Tester (MTT160) was utilized to assess the wet combing performance of aqueous polymer solutions of the current invention. The data in FIG. 2 was collected using the following general procedure. Individual hair tresses were prepared using 2.2 g of 8" white bleached hair and washed using SLES. An aqueous solution containing 0.5% polymer solids was prepared for each test material and adjusted to pH 6.0. Baseline measurements of the combing force for each hair tress were recorded using the Dia-Stron. Tresses were then treated with the pertinent 0.5% polymer solutions and rinsed with deionized water. The combing force was again measured and recorded. Baseline and post treatment results were then used to calculate the % reduction in the average combing force for each tress.

Figure 2:
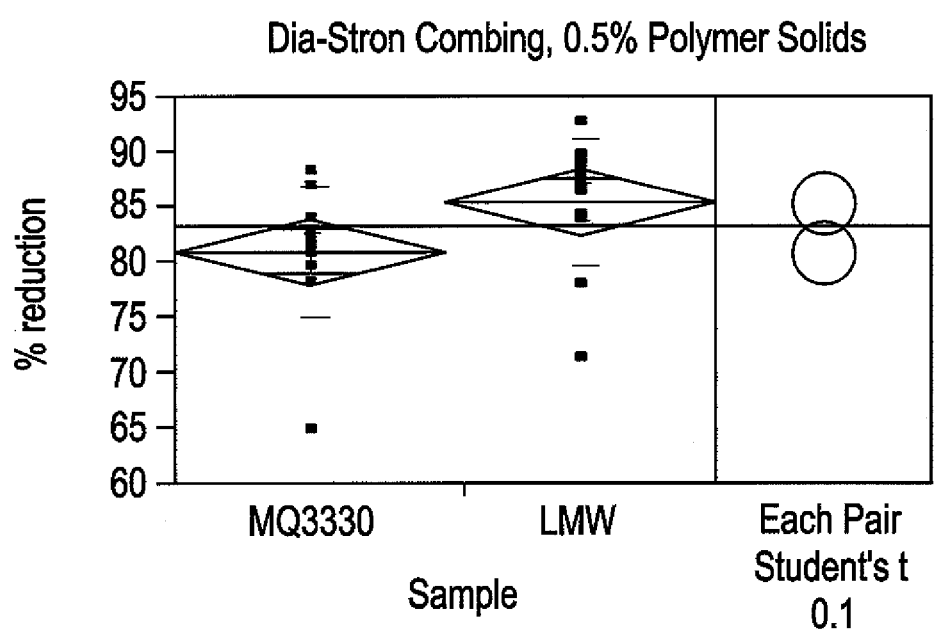
FIG. 2 shows combing force measurement in which hair tresses treated with LMW showed an 85.3% reduction in the force required to comb versus water baseline as compared to Merquat® 3330, which showed an 80.9% reduction.

Results for Merquat® 3330 and LMW are provided in FIG. 2. These are the same two polymers described in Example II. FIG. 2 shows that LMW showed an 85.3% reduction in the force required to comb versus water baseline as compared to Merquat® 3330 which showed an 80.9% reduction. This data is statistically significant at the 90% confidence level.

What is claimed is:

1. A cosmetically acceptable composition comprising from about 0.1 to about 10 weight percent, based on polymer solids, of an ampholyte polymer comprising:

(a) from at least 36 to as much as 40 weight percent of the nonionic monomer acrylamide of the following formula:

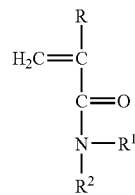

where R is H or $CH_3$; and $R^1$ and $R^2$ are independently H, $C_{1-4}$ alkyl, $CH_2OCH_3$, $CH_2OCH_2CH(CH_3)_2$, $(CH_2CH_2O-)_x-H$, where x=1-50, or phenyl, or together are $C_{3-6}$ cycloalkyl;

(b) from at least 15 to as much as 29 weight percent of the cationic monomer dimethyldiallylammonium chloride of the following formula:

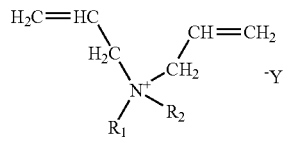

where $R_1$ and $R_2$ are independently H or $C_{1-12}$ alkyl, and the moiety $^-Y$ is a suitable anion;

(c) from at least 31 to as much as 40 weight percent of the anionic monomer acrylic acid of the following formula:

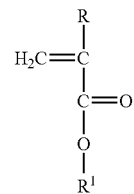

where R is H or $CH_3$; and $R^1$ is $X^+$, H, and $X^+$ is a suitable cation forming a salt of the carboxylic acid; and wherein the weight average molecular weight of said polymer is from about 5 thousand to about 250,000.

2. The cosmetically acceptable composition of claim 1 wherein said weight average molecular weight is from about 78,000 to about 165,000.

3. The cosmetically acceptable composition of claim 1 wherein said weight average molecular weight is about 150,000.

4. The cosmetically acceptable composition of claim 1 further comprising one or more excipients selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines of about $C_{10}$ to $C_{22}$, long chain fatty amines of about $C_{10}$ to $C_{22}$, fatty alcohols, ethoxylated fatty alcohols and di-tail phospholipids.

5. The cosmetically acceptable composition of claim 1, wherein the composition is in the form of a shampoo, aftershave, sunscreen, lotion, hand and body cream, liquid soap, bar soap, bath oil bar, shaving cream, dishwashing liquid, conditioner, permanent wave, hair relaxer, hair bleacher, hair detangling lotion, styling gel, styling glaze, spray foam, styling cream, styling waxer, styling lotion, mousse, spray gel, pomade, shower gel, bubble bath, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes or balms.

6. A method of treating a keratinous substance comprising applying the cosmetically acceptable composition of claim 1.

7. The method of claim 6, wherein said weight average molecular weight is from about 78,000 to about 165,000.

8. The method of claim 6, wherein said weight average molecular weight is about 150,000.

9. The method of claim 6, wherein said keratinous substance is hair or skin.

10. A method of treating a keratinous substance comprising applying a cosmetically acceptable composition comprising from about 0.1 to about 10 weight percent, based on polymer solids, of an ampholyte polymer produced by the following process:
   (1) preparing a monomer solution containing:
      (a) from at least 36 to as much as 40 weight percent of the nonionic monomer acrylamide of the following formula:

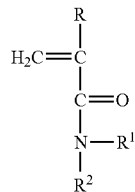

where R is H or $CH_3$; and $R^1$ and $R^2$ are independently H, $C_{1-4}$ alkyl, $CH_2OCH_3$, $CH_2OCH_2CH(CH_3)_2$, $(CH_2CH_2O-)_x$—H, where x=1-50, or phenyl, or together are $C_{3-6}$ cycloalkyl;

(b) from at least 15 to as much as 29 weight percent of the cationic monomer dimethyldiallylammonium chloride of the following formula:

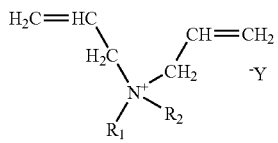

where $R_1$ and $R_2$ are independently H or $C_{1-12}$ alkyl, and the moiety $^-Y$ is a suitable anion;

(c) from at least 31 to as much as 40 weight percent of the anionic monomer acrylic acid of the following formula:

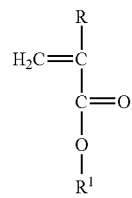

where R is H or $CH_3$; and $R^1$ is $X^+$, H, and $X^+$ is a suitable cation forming a salt of the carboxylic acid;

(2) providing a reactor and water to said reactor;
(3) optionally charging said reactor with a sequestering agent, a chain transfer agent or a combination thereof;
(3) purging said reactor to remove oxygen from said reactor;
(4) heating the contents of said reactor; and
(5) feeding said monomer solution and initiator solution into said reactor.

* * * * *